United States Patent [19]

Lee

[11] Patent Number: 4,666,851

[45] Date of Patent: May 19, 1987

[54] SPECIFIC MYCOPLASMA MEMBRANE ANTIGEN AND ANTIBODY AND THEIR CLINICAL APPLICATIONS

[76] Inventor: Sin H. Lee, 53 Milan Rd., Woodbridge, Conn. 06525

[21] Appl. No.: 726,987

[22] Filed: Apr. 25, 1985

[51] Int. Cl.[4] ............................................. C12N 1/20
[52] U.S. Cl. ...................................... 435/253; 435/7; 435/29; 435/170; 435/243; 435/261; 435/870; 436/518
[58] Field of Search ................. 424/3; 435/7, 29, 170, 435/243, 261, 253, 870; 436/518

[56] References Cited

U.S. PATENT DOCUMENTS 4,001,583  1/1977  Barrett .

OTHER PUBLICATIONS

Weir, D. M., Handbook of Experimental Immunology, 3rd ed., (1979), p. 28.20, Blackwell Sci. Pubs.
Kohler et al., Nature, vol. 256, (1975), pp. 495–497.
Textbook of Medicine, by P. B. Beeson and W. McDermott, W. B. Saunders Co., Philadelphia, 1975, pp. 270–274.
Medical Microbiology and Infectious Diseases, by A. I. Braude, W. B. Saunders Co., Philadelphia, 1981, pp. 925–929.
Respiratory Infections: Diagnosis and Management, by J. E. Pennington, Raven Press, New York, 1983, pp. 251–257.
Chanock, R. M., Hayflick, L. and Barile, M. F.; Proc. Nat. Acad. Science, 48:41–49, 1962.
Sillis, M. and Andrews, B. E.: A Simple Test for Mycoplasma Pneumoniae IgM Zentralblatt fur Bakteriologie, I. Abteilung Original, 241:239–240, 1978.
Buck, D. W., Kennett, R. H., and McGarrity, G.: Monoclonal Antibodies Specific for Cell Culture Mycoplasmas, In vitro, 18:377–381, 1982.
Lind, K., Lindhardt, B., Journal of Clinical Microbiology, Dec. 1984, pp. 1036–1043, "Serological Cross-Reactions between Mycoplasma genitalium and Mycoplasma pneumoniae".
Furr, P. M., and Taylor-Robinson, D.: "Microimmunofluorescence Technique for Detection of Antibody to Mycoplasma Genitalium", J. Clin. Path. 37:1072–1074, 1984.
Boatman, E. S., and Kenny, G.: "Morphology and Ultrastructure of Mycoplasma Pneumoniae Spherules", J. Bacteriology 106:1005–1015, Jun. 1971.
Carter, J. B. and Carter, S. L.: "Acute-Phase, Indirect Fluorescent Antibody Procedure for Diagnosis of Mycoplasma Pneumoniae Infection", Annals of Clinical and Laboratory Science, 13:150–155, 1983.
MP-1-IgM. Zeus TM Technologies, Inc., Series No. 17000 M. 1984.
Liu, C.: J. Experimental Medicine 106:455–466, 1957.
Kenny, G. E. and Grayston, J. T., The Journal of Immunology 95:19–25, 1965.
The Mycoplasmas—Cell Biology, Ed. M. F. Barile and S. Razin, Academic Press, New York, 1979, pp. 315–319.
"ELISA: a Replacement for Radioimmunoassay?", The Lancet, Aug. 21, 1976, pp. 406–407.
Methods in Enzymology, vol. 73, pp. 234–235, 1981.
S. Avrameas, Immunochemistry, vol. 6, pp. 43–52, 1969.
J. B. Baseman, et al, "Absence of Mycoplasma Pneumoniae Cytadsorption Protein P1 in Mycoplasma genitalium and Mycoplasma Gallisepticum", Infection and Immunity, Mar. 1984, pp. 1103–1105.
J. Feldner, U. Gobel & W. Bredt, "Mycoplasma Pneumoniae Adhesion Localized to Tip Structure by Monoclonal Antibody", Nature, vol. 298, Aug. 19, 1982.
Hu, et al, "Mycoplasma Pneumoniae Infection: Role of a Surface Progein in the Attachment Organelle", Science, vol. 216, Apr. 16, 1982, pp. 313–315.

Primary Examiner—Christine M. Nucker
Assistant Examiner—Stephen C. Wieder
Attorney, Agent, or Firm—Cushman, Darby & Cushman

[57] ABSTRACT

A method to produce actively growing mycoplasma organisms in microcolonies and which have a high content of species specific membrane antigen, is disclosed. The specific membrane antigen can be used to detect specific antibodies against mycoplasma in a patient's serum samples. It can also be used to elicit antibody production in animals so that the specific membrane antigen of mycoplasma can be detected using animal antibody tracers, in the sputum of patients having a mycoplasma infection.

10 Claims, No Drawings

SPECIFIC MYCOPLASMA MEMBRANE ANTIGEN AND ANTIBODY AND THEIR CLINICAL APPLICATIONS

BACKGROUND OF THE INVENTION

Mycoplasmas are the smallest free-living microorganisms known to man. They are smaller than bacteria and larger than most viruses, measuring about 10×200 nm in size. Because they lack a rigid cell wall, are very pleomorphic and stain poorly with dyes, the individual organisms are very difficult to recognize with light microscopy. In fact, the species Mycoplasma pneumoniae (M. pneumoniae), a pathogen causing human primary atypical pneumonia and upper respiratory tract infections, was initially given such ill-defined names as Eaton agent and pleuropneumonia-like organism (PPLO). Cultivation of the organism in cell-free media was not achieved until early 1960s. Methods for isolation, propagation and specific identification of M. pneumoniae from patients' excretions remain highly technical and are performed routinely only in a few laboratories. Most clinical laboratories depend on either nonspecific serologic tests, such as cold agglutinin and MG streptococcus tests, or the complement fixation test for establishing diagnosis of M. pneumoniae infections in humans. [Textbook of Medicine, by P. B. Beeson and W. McDermott, W. B. Saunders Co., Philadelphia, 1975, pp. 270-274. Medical Microbiology and Infectious Diseases, by A. I. Braude, W. B. Saunders Co., Philadelphia, 1981, pp. 925-929. Respiratory Infections: Diagnosis and Management, by J. E. Pennington, Raven Press, New York, 1983, pp. 251-257.]

Several investigators have attempted to use an indirect fluorescent antibody technique, using M. pneumoniae grown in solid or liquid media as antigens. In 1962 Chanock, Hayflick and Barile reported successful transferring of mycoplasmal colonies from solid agar media to glass slides and demonstrating specific antibodies against these colonies in convalescent serum samples of patients recovering from M. pneumoniae infection. [Chanock, R. M., Hayflick, L. and Barile, M. F.; Proc. Nat. Acad. Science, 48:41-49, 1962.] However, because the colonies of the microorganisms are largely embedded in the agar and not readily removed by mechanical scraping, the researchers had to place the agar medium with grown colonies on the slide, then melted the agar away by raising its temperature to at least 80° to 85° C. in order to remove the agar. Unfortunately, by doing so the antigen is partially denatured, and the technique cannot be used to produce a large number of slides with adherent colonies for diagnostic purpose in a clinical laboratory.

In 1978, Silis and Andrews suggested using the granular deposits from a liquid culture of M. pneumoniae as antigen for the indirect fluorescent antibody test instead of colonies grown in a solid medium so that the heating procedure can be omitted. These granular deposits were presumably mycoplasmal colonies. [Silis, M. and Andrews, B. E.: A simple test for Mycoplasma pneumoniae IgM. Zentralblatt für Bakteriologie, I. Abteilung Original, 241:239-240, 1978.] However, this approach has not been widely used because antigenic specificity of these deposits or whole colonies has not been proven. In fact, there is significant antigenic cross reaction between M. pneumoniae and M. genitalium colonies. [Lind, K., Lindhardt, B., Schütten, H. J., Blom, J. and Christiansen, C.: Serological Cross-Reactions between Mycoplasma Genitalium and Mycoplasma Pneumoniae, J. Clinical Microbiology 20: 1036-1043, 1984.]

Another approach to procure M. pneumoniae antigen for indirect fluorescent antibody test in a clinical laboratory is to use a commercial M. pneumoniae preparation which has been grown in a liquid medium, centrifuged and freeze-dried, and marketed by Wellcome Laboratories, Research Triangle Park, N.C., U.S.C., as reported by Carter and Carter. [Carter, J. B. and Carter, S. L.: Acute-Phase, Indirect Fluorescent Antibody Procedure for Diagnosis of Mycoplasma Pneumoniae Infection. Annals of Clinical and Laboratory Science, 13:150-155, 1983.] Unfortunately, by using this material as antigen, the authors reported that "a positive result appears as an applegreen, fluorescent slurry of particulate matter consistent with the almost submicroscopic morphology of the M. pneumoniae organism" (p. 152). In other words, the authors found it difficult to distinguish M. pneumoniae organisms from other particulate matters from the liquid media with confidence. It has been well-recognized by workers in the field of mycoplasma research that precipitates other than mycoplasma organisms invariably form in the agitated liquid media during incubation. The precipitates are not readily distinguishable from the highly pleomorphic minute microorganisms. Serum samples containing high titer of non-specific immunoglobulin M such as rheumatoid factors, may give rise to false positive results. [MP-1-IgM. Zeus ® Technologies, Inc., Series No. 17000 M. 1984 (see "Limitations", No. 6), P. O. Box 177, Raritan, N.J. 08869.]

From these earlier publications by others, it has become clear that the only reliable morphologic criterion for recognizing the M. pneumoniae organisms is by its colony-forming characteristic, i.e., to work with concentrated, purified microcolonies. However, the whole colonies may contain non-specific antigens. Therefore, one must use colonies with abundant species-specific antigens which can be distinguished morphologically from non-specific antigens.

It is an object of the present invention to provide a method for selective propagation of colony-forming mycoplasma in dialysed, particle-free liquid media by "weeding out" the single growing units through a series of subcultures.

It is another object of the invention to provide a method for making an inoculum by breaking up of the tuberous floating colonies of mycoplasma by gentle homogenization into small fragments, but not into single growing units. The inoculum is used for the last culture in which each fragment grows into a medusoid in 4-5 days.

Another object of the invention is the identification of specific membrane antigen.

It is a further object of the invention to use aldehydes, desirably glutaraldehyde to stabilize the specific membrane antigens of mycoplasma.

SUMMARY OF THE INVENTION

The present invention provides a method to produce large quantities of actively growing mycoplasma organisms in microcolonies or medusoids which can be identified microscopically with ease and have a high content of species-specific membrane antigen. The specific membrane antigen can be used to detect specific antibodies against mycoplasma in patient's serum samples. It can also be used to elicit antibody production in animals so that the specific membrane antigen of mycoplasma can be detected using the animal antibodies as tracers, in the sputum of patients having a mycoplasma infection.

DETAILED DESCRIPTION OF THE INVENTION

The present invention is related to a test using a technique for massive propagation of mycoplasma colonies with a species-specific membrane antigen, and an approach enabling the recognition of a specific antigen-antibody reactions with these antigens or antibodies.

The importance of an immunofluorescence method for detection of mycoplasma organisms and their antibody is emphasized by its role in establishing the causative relationship between Mycoplasma pneumoniae and primary atypical pneumonia in humans. [Liu, C. : J. Experimental Medicine 106:455-466, 1957.] The test appears to be species specific under optimum conditions in the hands of experts.

Acetone, a common solvent fixative for preparation of immunofluorescence antigens, tends to remove the specific membrane antigen from these peripheral cells. In order to preserve the membrane antigen on glass slides, the mycoplasma medusoids must be fixed by non-solvent fixatives, such as aldehydes. The aldehyde employed is not critical for operative results; glutaraldehyde is presently the aldehyde of choice. Other aliphatic aldehydes may be used such as formaldehyde, paraformaldehyde and dialdehydes such as adipaldehyde. Using these aldehyde-fixed medusoids as antigen, immunoglobulins M and G antibodies specific for M. pneumoniae membrane can be detected in the serum samples of patients suffering from M. pneumoniae infection or in immune serum of rabbits immunized with M. pneumoniae medusoids.

Other investigators have used organic solvents, in particular acetone, as fixatives to inactivate and preserve the mycoplasma antigen either in the form of whole colonies (granular deposits) or as slurry. The present invention is in part developed from the recognition that this traditional approach has at least two conceptional and technical flaws.

Firstly, some important components, such as the glycolipids in the mycoplasma membrane, would be removed by the organic solvents. Structurally located at the surface of the microorganism, the membrane antigens must play the most important role in the initial interaction with the susceptible cells of a host. Removal of the glycolipids invariably disrupts the integrity of the antigenic determinants of the membrane. The major antigen of M. pneumoniae, as measured by both rabbit immune and human convalescent serum, has been found in the lipid fraction of the organisms. [Kenny, G. E. and Grayston, J. T., J. Immunol. 95:19-25, 1965, especially pp. 23-24.]

Secondly, the use of whole colonies or culture slurry as the antigen fails to take into consideration the age of the mycoplasma microorganisms. The process of aging in mycoplasma culture is known to be accompanied by a marked decrease in the activity of membrane-associated enzymes and by an increase in the protein:-lipid ratio in the membrane fraction isolated from the osmotically-lysed cell suspensions, suggesting that the young organisms must contain physiologically more active and more lipid-rich membranes than the older cells [The Mycoplasmas—Cell Biology, Ed. M. F. Barile and S. Razin, Academic Press, New York, 1979, pp. 315-319.] Because of the long replication time, each colony or granule recovered from a mycoplasma culture (usually at least several days old) is invariably composed of organisms of various ages. The youngest cells in logarithmic phase of replication are logically the most valuable organisms to provide the most specific membrane antigen.

This new technology is based on the discovery that mycoplasma, such as M. pneumoniae, can be selectively cultivated in the form of tuberous floating colonies, or in the form of medusoid microcolonies when fragments of the tuberous floating colonies are incubated in a fresh medium for about 5 days. A single growing unit cannot form a medusoid in this short time because of the slow growth rate of M. pneumoniae. In these selected cultures, individual or isolated growing units of the mycoplasma organisms are kept to a relatively small number so that their competition with the floating colonies or medusoids for nutrients or for other growth factors is minimized. The mycoplasma organisms grown in this manner can be recognized easily under the microscope because they present themselves in the form of characteristic colonies. Since the base of the media has been dialyzed, and the horse serum has been filtered, and the incubation is carried out without agitation, no particulate matters are formed in these cultures other than microorganisms.

Although the membranes of mycoplasma have been known to be the most important structure of the microorganism, prior approaches have used chemical analyses to study the membranes, their ingredients, and the antigenicity of their chemical ingredients. These earlier techniques ignore the fact, here recognized, that only the very young cells, i.e. of only a few hours to one-day-old, at the growing edge of a colony or a medusoid, contain the specific membrane antigen. Chemical analysis of the membrane fractions, isolated from a whole culture or from an entire colony population, cannot distinguish the specific membrane antigen from the non-specific components. The entirely new technique of this invention deals with the antigenicity of the intact membrane of the very young M. pneumoniae polyps or vesicles, polysaccharides, proteins and lipids included in their natural spatial relationship.

Specific M. pneumoniae membrane antibody has been produced by immunizing rabbits with medusoids of M. pneumoniae and the non-specific antibodies can be removed by absorption with acetone-fixed colonies harvested from old M. pneumoniae cultures. Using the absorbed specific antibody, M. pneumoniae membrane antigens in sputum can be detected either by an ELISA (enzyme-linked immunosorbent assay), [Lancet, Aug. 21, 1976, pp. 406-407] or by an immunofluorescence technique.

The clinical application of this new technology can improve the accuracy in early diagnosis and early treatment of M. pneumoniae infection. Identification of specific membrane IgM antibody or observation of a rising titer of specific membrane IgG antibody in the patient's serum indicates that the patient is having or has just recovered from an acute active infection caused by M. pneumoniae. Serologic or immunofluorescent identification of the M. pneumoniae antigen or the characteristic membrane-delineated growing units in the sputum or sputum culture also indicates active proliferation of this microorganism in the upper respiratory tract, presumably evidence for an acute infection.

This invention further provides the potential for the development of monoclonal antibodies specifically against mycoplasma membrane antigens, using existing hybridoma techniques. In this case, the glutaraldehyde fixed medusoids provided here can be used as the antigen for selecting the hybridoma cell lines that produce the specific monoclonal antibody against the membrane of the polyps or vesicles.

The invention will now be elucidated by means of the following examples which will illustrate the practice of the invention, without the same being limited thereto.

EXAMPLE A

I. Preparation of Media

1. The following ingredients are placed in a semipermeable tubing.

| | |
|---|---|
| Broth base, PPLO Broth Base (Difco Lab.) | 210 gm |
| Yeast extract, Yeastolate (Difco Lab. | 30 gm |
| Thallium acetate | 412.5 mg |
| Distilled water | 1,000 ml |

2. The tubing is dialyzed in distilled water, total volume 10 liters including tubing contents, for three days at 2°–5° C.

3. The tubing and contents within are then discarded. The volume of dialysate is then about 8,500 ml.

4. The dialysate is adjusted to a pH of about 7.8 with 1 N NaOH, and filtered through filter paper to remove any traces of particles.

5. Next, the dialysate is sterilized in an autoclave at 121° C. for 20 minutes.

6. The final medium is then prepared so as to consist of 80 ml of dialysate, 20 ml of filtered gamma-globulin-free horse serum and 500 units of penicillin per ml, or any overall amount thereof in the same general proportion of the ingredients.

II. Selective Isolation of Tuberous Floating Colonies of M. Pneumoniae

A stock culture of a standard strain of M. pneumoniae is inoculated in a test tube containing about 10 ml of liquid medium, and incubated at 37° C. with slow rotation for four days. About 0.5 ml of the initial culture is transferred to a second test tube with fresh medium at the end of the four-day incubation. About three serial subcultures in this manner will produce actively growing microorganisms of M. pneumoniae in the liquid medium. After a four-day incubation in the last subculture, the liquid culture is left in the incubator without further rotation or agitation for 2–3 weeks. The sediment in the medium is sampled and observed for the appearance of tuberous floating colonies of M. pneumoniae of about 25–50 μm in diameter microscopically. When their presence is confirmed, the sediment is resuspended and the suspension is centrifuged at a speed of 1,500 r.p.m. for 20 minutes. The supernatant liquid is then replaced with fresh liquid medium, and the sediment is incubated further for about seven days while being mixed by inverting the test tube once a day. The supernatant liquid is replaced with fresh medium every seven days. After about 3 weeks, tuberous floating colonies of mycoplasma become the prevalent form of growth, many forming conglomerates of over 100 μm in diameter. They are then transferred into larger tissue culture flasks with flat bottoms for further propagation.

III. Formation of Medusoid Microcolonies in Liquid Media

About 500 tuberous floating mycoplasma colonies which have been incubated in a fresh liquid medium for 4–5 days and harvested by centrifugation, are transferred to a Potter-Elvehjem glass tissue grinder containing about 2 ml of liquid medium, and homogenized with a Teflon pestle driven by a motor turning at 100–200 r.p.m. for no more than one minute. At the end of homogenization, all colonies should have been disintegrated; this can be confirmed microscopically. Then the homogenate is mixed with about 50 ml of fresh medium and incubated in tightly capped plastic Petri dishes or plastic tissue culture flasks with flat bottom. The medium in the culture is adjusted to about 3 mm in height. After a 5-day incubation at 37° C., round or ovoid microcolonies most of them ranging from 5 to 25 μm in diameter are formed in the liquid culture either floating freely or loosely attached to the bottom of the container. The attached colonies are gently rinsed off the bottom with phosphate-buffered saline, pH 7.4 (PBS). The microcolonies are then harvested by low-speed centrifugation.

After three washes in PBS, drops of a heavy suspension of microcolonies are placed on glass slides and dried at room temperature. They can now be used as unfixed antigen preparations or preferably used after fixation in 1% glutaraldehyde in PBS for 2 minutes. Since these microcolonies are composed principally of numerous tiny polyps or vesicles, 2–12 μm in size that are delineated by membranes of 0.1–0.2 μm thick after immunofluorescent staining, and since they almost invariably surround a closely packed core of apparently less active organisms (thus resembling small jellyfish), they are referred to here as medusoid microcolonies, or medusoids.

IV. Indirect Immunofluorescence Test for Specific Antimycoplasma Antibodies in Patient Serum The serum samples of patients to be tested for a mycoplasma infection are diluted serially with a 2-fold dilution method, with PBS to 1:10, 1:20, 1:40, 1:80, 1:160 etc. One drop of the respective diluted serum samples is first reacted with the mycoplasma medusoid microcolonies dried on the slides as antigen. After washing off the patient serum, the antigen is then covered with a fluoresceinated anti-human IgG or IgM antibodies raised in animals (rabbit, goat, sheep, swine, etc.). After the unbound fluorescent antibodies are washed off, the slides are mounted in buffered glycerin. The thus prepared and reacted microcolonies are then examined with a fluorescence microscope to determine the membrane fluorescence characteristics of the microcolonies.

When a significant concentration of M. pneumoniae antibodies (IgG or IgM or both) is present in the patient serum, the membranes and only the membranes of these polyps or vesicles at the surface or the periphery of the medusoids will fluoresce. The quantity of the antibodies is then reflected by the titer (dilution). The membranes of the medusoid reacted with normal or control serum samples do not fluoresce and are therefore not visible.

(a) Comparison with aged colony cultures

When the floating colonies are allowed to age in the culture for three weeks or longer, the young mycoplasma cells at the periphery can no longer be demonstrated by the immunofluorescence technique, indicating that the specific membrane antigen has largely disappeared. However, these old colonies are not dead because actively growing vesicular cells with specific membrane antigen may grow out at the surface of these colonies after they are re-incubated in fresh media for two to four days.

(b) Comparison with fixed culture after acetone immersion

The specific membrane antigen of the medusoid which has been fixed in glutaraldehyde can no longer be demonstrated after the antigen preparations are immersed in acetone for 2 minutes.

V. Production of antibodies

In order to produce antibodies against the specific membrane antigen of M. pneumoniae, washed live M. pneumoniae medusoid microcolonies of a 4-day culture are injected intravenously into rabbits at a 10-14 days interval. After six to seven injections, the serum samples of the immunized rabbits are tested for antibodies against the specific membrane antigens, using the above-described immunofluorescence technique. The binding of the IgG and IgM antibodies to the membrane of the mycoplasma medusoid microcolonies is demonstrated by fluorescent goat antirabbit immunoglobulin antibody. The rabbit immunoglobulins are isolated by the standard ammonium sulfate technique. The nonspecific antibodies, which are directed against the cytoplasm and the inactive forms of the mycoplasma cells, are absorbed by washed acetone-fixed tuberous colonies of a 4-weeks-old culture. After absorption, the rabbit immunoglobulins are highly specific for the membrane antigen of M. pneumoniae, and can be used to detect the soluble or membrane antigens of M. pneumoniae in the sputa and other exudates.

One such example is illustrated as follows:

EXAMPLE B

1. Specimen preparation

A thick smear of sputum of patients with M. pneumoniae infection or of sputum containing M. pneumoniae grown in the laboratory is allowed to dry on a watch glass at 37° C. (in one hour). The dried smear is extracted by acetone (2-5 ml). The acetone extract is transferred to a glass test tube, and the solvent is evaporated at about 37° C. by inserting the test tube in a heating block. One ml of PBS, pH 7.4, containing 1% bovine serum albumin (BSA) is added and mixed with the residue, and the test tube is shaken in a 37° C. water bath for one hour to obtain the soluble lipid fraction. The insoluble residue is discarded as sediments after centrifugation.

2. Preparation of antibody-coated test tubes or membrane filters

The glutaraldehyde-treated test tube method (M. J. Barrett, et al., U.S. Pat. No. 4,001,583, as quoted in Methods in Enzymology, Vol. 73, p. 234-235, 1981) is followed. With this method, the specific M. pneumoniae membrane antibody (rabbit immunoglobulins) is bound to the bottom of polypropylene test tubes. Alternatively, a commercially available protein-binding membrane, such as Pall Biodyne ® Immunoaffinity Membrane (Biotechnology Division, Pall Ultrafine Filtration Corporation, Glen Cove, N.Y. 11542), can be used. The purpose is to make the antibody adhere to a solid surface while preserving its specific antigen-binding activity.

The following steps are next performed:

(a) Incubate the soluble lipid fraction of the sputum with the antibody immobilized on the plastic tube surface or on the membrane filter for 30 minutes at room temperature.

(b) Wash the test tube or membrane thoroughly with PBS.

(c) Add an enzyme-labeled rabbit M. pneumoniae specific antibody (see above) carrying an alkaline phophatase covalently bound to the immunoglobulin molecules (S. AVRAMEAS, Immunochemistry, Vol. 6, pp. 43-52, 1969) to the test tubes or membranes.

(d) After incubation for 30 minutes, the unbound phophatase-labeled antibody is rinsed off with a Tris-HCl buffered saline, pH 7.4. The bound labeled antibody is quantificated with a standard Bodansky or other method for alkaline phophatase. The presence of high alkaline phophatase activity indicates a high titer of acetone-extractable M. pneumoniae antigen in the patient's sputum. The control specimens without M. pneumoniae should be negative.

EXAMPLE C

Another example of using the specific antibody to detect M. pneumoniae specific membrane antigen in sputum or other exudates directly or after incubation in a liquid medium, is to stain the sputum smear or the sediment of a liquid culture of sputum with an indirect immunofluorescence technique. In this method, the smear of sputum or the sediment of a liquid culture of sputum on a microscopic slide is first air dried and fixed with 1% glutaraldehyde in PBS at pH 7.4 for 2 minutes. The specific rabbit anti-M. pneumoniae immunoglobulins are first allowed to react with the smear, and the bound immunoglobulins are then visualized with a fluorescent goat antirabbit gamma-globulin antibody (by the methods described above). If a polyp or vesicular microorganism of 2-12 $\mu$m in diameter, arranged in clusters like "medusoid" and delineated by the specifically stained membrane is found, a diagnosis of the presence of M. pneumoniae in the sputum can be made.

It should be noted that the above procedures are also applicable to other mycoplasma infections such as Mycoplasma genitalium.

While the invention has now been described in what are considered to be the preferred embodiments, it should be understood that the invention is not limited to the disclosed embodiments but, is intended to cover various modifications and equivalent processes included within the spirit and scope of the appended claims, which claim scope is to be accorded the broadest interpretation so as to encompass all such modifications and equivalent processes.

What is claimed is:

1. A method for producing actively growing mycoplasma organisms in microcolonies for subsequent antigen-antibody identification, and which have a high content of species-specific membrane antigen, comprising:
   (a) forming a culture of a standard strain of mycoplasma in a dialysed, particle free liquid medium, and incubating said culture therein;
   (b) transferring a resulting portion of said incubating culture to a fresh batch of said liquid medium, and again incubating the same therein to form a subculture;

(c) repeating step (b) at least once to provide at least 3 total incubations and a final subculture;

(d) incubating said final subculture for a period of time sufficient to form tuberous colonies of mycoplasma of about 25–50 $\mu$m diameter;

(e) separating said tuberous colonies and reincubating the same in successive fresh batches of medium until tuberous floating colonies of mycoplasma are the predominent growth form;

(f) harvesting said tuberous floating colonies, homogenizing the same, and re-incubating in fresh medium to form round or ovoid microcolonies of from 5 to 25 $\mu$m diameter; and (g) harvesting and washing the same to obtain medusoid microcolonies composed of polyps or vesicles of 2–12 $\mu$m in diameter delineated by membranes.

2. A method as in claim 1 wherein said mycoplasma is M. pneumoniae.

3. A method as in claim 1 wherein said mycoplasma is M. genitalium.

4. A method as in claim 1 wherein the harvested medusoid microcolonies are subsequently fixed in an aliphatic aldehyde.

5. A method as in claim 4 wherein the aldehyde is glutaraldehyde.

6. A method as in claim 1 wherein said harvesting is done by centrifugation.

7. A method as in claim 1 wherein said liquid medium comprises: (1) a sterilized dialysate of broth, yeast extract, thallium acetate and distilled water, (2) gamma-globulin-free horse serum, and (S) penicillin, wherein said liquid medium is adjusted to a pH between 7.0–7.8.

8. A method for producing tuberous floating colonies of mycoplasma organism comprising the steps of:

(a) dialyzing broth, yeast extract, thallium acetate and distilled water;

(b) adjusting the dialysate to about pH 7.0–7.8;

(c) filtering said dialysate to remove any traces of particles;

(d) sterilizing said dialysate;

(e) preparing a liquid medium of said dialysate, gamma-globulin-free horse serum, and penicillin;

(f) forming a culture of a standard strain of mycoplasma and said liquid medium;

(g) incubating and slowly rotating said culture therein;

(h) transferring a resulting portion of said incubating and rotating culture to fresh batch of said liquid medium, and again incubating the same therein to form subcultures;

(i) repeating step (h) at least once to provide a least 3 total incubation and a final subculture;

(j) incubating said final subculture for a period of time sufficient to form tuberous colonies of mycoplasma of about 25–50 m diameter, without rotation or agitation; and (k) separating said round colonies and reincubating the same in successive batches of liquid medium until tuberous floating colonies of mycoplasma are the predominant growth form.

9. A method as in claim 8 wherein said mycoplasma is M. pneumoniae.

10. A method as in claim 8 wherein said mycoplasma is M. genitalium.

* * * * *